United States Patent
Evans et al.

(12)

(10) Patent No.: US 6,284,711 B1
(45) Date of Patent: Sep. 4, 2001

(54) USE OF A SEMICARBAZONE PLANT GROWTH REGULATOR FOR EARLY TERMINATION OF CROP PLANTS

(75) Inventors: John R. Evans, Raleigh, NC (US); Wallace W. Stewart, Brandon, MS (US); Thomas J. Holt, Holly Springs; David M. Saravitz, Apex, both of NC (US); Richard R. Evans; Lisa P. Evans, both of Greenville, MS (US)

(73) Assignee: BASF Corporation, Mount Olive, NJ (US)

( * ) Notice: Subject to any disclaimer, the term of this patent is extended or adjusted under 35 U.S.C. 154(b) by 0 days.

(21) Appl. No.: 09/461,382

(22) Filed: Dec. 15, 1999

(51) Int. Cl.⁷ ...................................................... A01N 43/00
(52) U.S. Cl. .......................... 504/244; 504/116; 504/246
(58) Field of Search ...................................... 504/116, 244

(56) References Cited

U.S. PATENT DOCUMENTS

| | | | | |
|---|---|---|---|---|
| 3,879,188 | * | 4/1975 | Fritz et al. | 71/86 |
| 5,098,462 | * | 3/1992 | Anderson et al. | 71/88 |
| 5,098,466 | * | 3/1992 | Anderson et al. | 71/94 |
| 5,123,951 | * | 6/1992 | See et al. | 71/86 |
| 6,090,750 | * | 7/2000 | Chollet et al. | 504/105 |

* cited by examiner

Primary Examiner—Sabiha N. Qazi
(74) Attorney, Agent, or Firm—Nixon & Vanderhye P.C.

(57) ABSTRACT

Late season termination of reproductive plant growth of a plant having an indeterminate growth pattern is achieved by the application of a semicarbazone plant growth regulator to a locus of a growing plant at a time following peak bloom of the plant. The semicarbazone is applied as an active ingredient in an amount sufficient to terminate continued reproductive growth of the plant without substantially affecting mature reproductive growth existing on the plant at the time of application. Most preferably, the semicarbazone is diflufenzopyr.

13 Claims, No Drawings

USE OF A SEMICARBAZONE PLANT GROWTH REGULATOR FOR EARLY TERMINATION OF CROP PLANTS

FIELD OF THE INVENTION

The present invention relates to the use of a semicarbazone plant growth regulator for the early termination of crop plants. More particularly, the present invention relates to the use of a semicarbazone plant growth regulator in order to improve late-season fruit yield and/or late-season pest management.

BACKGROUND AND SUMMARY OF THE INVENTION

Plant growth regulators (PGR's) affect the physiology of plant growth and influence the natural rhythm of a plant. More specifically, plant growth regulators may, for example, reduce plant height, stimulate seed germination, induce flowering, darken leaf coloring, minimize lodging of cereals, slow grass growth on lawns, reduce boll rot and improve boll retention in cotton.

Crop plants generally display a determinate or indeterminate growth pattern. Determinate plants have a defined period of vegetative growth followed by a defined interval of reproductive growth in which there is a maximum number of flowers initiated per plant. An indeterminate plant growth pattern, on the other hand, is characterized by an initial period of vegetative growth followed by a period where both vegetative and reproductive growth occur together. The length of the second period and the number of flowers produced are determined largely by the growing conditions.

Indeterminate crop plants continue to produce reproductive organs long past the point in the growing season where there is sufficient time for mature, harvestable fruit to be obtained from these organs. Thus, after a certain point in the growing season, further reproductive growth will have no impact on marketable yield. Because flowers and young fruit are strong sinks for carbohydrates and nitrogen, it is likely that the demand of these strong sinks causes a reduction in the available carbohydrates and nitrogen for the continued maturation of fruits that are far enough along in development to make a positive contribution to marketable yield.

Young, expanding leaves are also strong nutrient sinks. As a leaf approaches physiological maturity, it changes from a carbohydrate sink to a carbohydrate source due to the combination of increased photosynthetic capacity within the leaf as well as a decline in, and eventually a cessation of, growth. For indeterminate plants, leaves initiated after a certain point in the growing season will lack sufficient time to make the transition from carbohydrate sink to carbohydrate source. Thus, young expanding leaves drain the finite nutrient and carbohydrate resources of the plant that might otherwise be better allocated to the growth and maturation of marketable fruit.

One example of an important crop plant that displays an indeterminate growth pattern is cotton (*Gossypium hirsutum*). Cotton is a perennial of tropical origin that is cultivated as an annual in agricultural production in temperate and subtropical regions of the world. After an initial period of vegetative growth, a cotton plant initiates reproductive growth while vegetative growth continues. Flower buds (squares) appear, develop into flowers, and after pollination, give rise to fruit that are referred to as bolls.

Due to its indeterminate nature, squares continue to appear long after there is sufficient time left in the growing season for these squares to develop into mature, marketable bolls. The growth and development of these squares and young bolls drains the limited resources of the plant that might better be utilized by bolls that have sufficient time to mature to a marketable stage. Likewise, the shoot of the cotton plant continues to grow and initiate new leaves throughout most of the growing season. Many of the leaves that are initiated late in the growing season will never become carbohydrate source leaves due to insufficient time remaining in the growing season. Thus, these young leaves demand a portion of the carbohydrates and other nutrients that could be better utilized by the bolls that are likely to be harvested.

The peanut plant (*Arachis hypogaea*), a member of the Fabaceae family, is another important crop plant which exhibits an indeterminate flowering pattern similar to cotton. Like cotton, peanut plants will produce flowers so late in the season that these late season flowers will not have the time to develop into a marketable fruit before the first frost.

Tobacco (*Nicotiana tabacum L.*) production requires the early removal of the terminal bud by a process called "topping". Removal of the terminal bud stimulates growth and development of the axillary buds (suckers) Suckers are of no economic value and, if allowed to develop, would decrease the leaf yield. Chemical control of suckers is practiced through the United States typically using maleic hydrazide.

If an early-termination, plant-management strategy could be developed that reduces the number of late-season squares, flowers and young fruit, as well as eliminate further growth of the terminal portion of the shoot, then the carbohydrates and other nutrients would be reallocated to the strongest sinks remaining—namely, the young fruit and/or leaves. For cotton plants, as an example, the benefits of this reallocation of resources is likely to include some, or all, of the following: increased yield (due to larger bolls), increases in fiber quality, an acceleration of boll opening, a more complete defoliation and the ability to harvest earlier. All of these benefits can provide cotton producers with a significant economic advantage.

For an early termination strategy to be successful, inhibition of both vegetative and reproductive growth would have to occur without substantial injury to organs, such as leaves, stems, roots and fruit. A herbicide treatment could be used to terminate growth, however, the injury to the crop plant would be severe and likely cause significant reductions in yield.

Early growth termination could also have benefits in terms of late season pest management. The recent introduction of transgenic, insect-resistant cotton cultivars that have been genetically modified to express the *Bacillus thurigensis* insect toxin (BT toxin) has reduced the necessity and/or frequency of some insecticide applications. However, so-called insect-resistant "BT-cotton" is not the panacea for insect management in cotton production. In this regard, the insect resistance of BT-cotton is limited to a subset of the major insect pests of cotton. In addition, the resistance provided by the presence of BT toxin in crop plants is not permanent. Unfortunately, there is evidence that some individual members of pests species otherwise susceptible to BT toxins may no longer be affected by the BT toxin.

Thus, insecticides remain a vital component of cotton production systems along with BT cotton. Because insects that are either resistant to currently known insecticides and/or tolerant to the BT toxin will increase over time, new insect management strategies need to be developed to ensure that the cotton production levels meet future demand.

As a means to both lower production costs and mitigate the development of insects with insecticide resistance, the elimination of late-season insecticide applications is currently being recommended by some cotton production experts. The basis of this recommendation is that after a certain point in the season, insect damage to flower buds (squares), flowers and young fruit (bolls) does not affect marketable yield. Due to the indeterminate nature of cotton, production of squares, flowers and bolls continues throughout much of the latter part of the growing season. However, after a certain point in the growing season there is insufficient time for squares, flowers and young bolls to mature and contribute to marketable yield with or without further insecticide applications. Because mature and near-mature bolls are not particularly susceptible to damage by the major insect pests of cotton, stopping insecticide applications later in the season might not significantly reduce yield. Although reducing late-season insecticide applications may make economic sense in the short term, the lack of late-season control one season will most likely lead to larger insect populations earlier in the next season.

Some key insect pests of cotton include the bollworm (*Helicoverpa zea*), tobacco budworm (*Heliothis virescens*) and boll weevil (*Anthonomus grandus*). In the case of bollworms and budworms, moths lay eggs usually in the terminal area (shoot apex) of the cotton plant. After hatching, young larvae feed on the terminals and younger squares, and larger larvae feed on terminals and young bolls. For the boll weevil, adult females eat a cavity into a square and lay a single egg. Upon hatching, the larvae feeds inside the square and undergoes two or three molts. Squares containing boll weevil larvae usually abscise from the plant and fall to the ground a few days after the development of the second stage larvae. Boll weevil development continues in the abscised square.

A crop management strategy that reduces or eliminates the feeding and/or oviposition sites of insect pests might eliminate the need for late-season insecticide applications and also lower the populations of overwintering insects. In the case of the boll weevil, a crop management strategy that reduces late season squares should reduce the overwintering boll weevil populations because it is known that boll weevils that enter diapause later in the season are more likely to overwinter successfully than boll weevils that enter diapause earlier.

It is towards providing a successful early-termination strategy which meets, or exceeds, the goals noted above that the present invention is directed. Broadly, the present invention is directed toward the late-season termination of reproductive plant growth of a plant having an indeterminate growth pattern. More particularly, according to the present invention, a semicarbazone plant growth regulator is applied to a locus of a growing plant at a time following peak bloom of the plant in an amount sufficient to terminate continued reproductive growth of the plant without substantially affecting mature reproductive growth existing on the plant at the time of application. Most preferably, the semicarbazone is diflufenzopyr. By using such an early growth-termination strategy, improvements in the plant's late-season fruit yield as well as improved late-season pest management may be achieved.

These and other aspects and advantages of the present invention will become more clear after careful consideration is given to the following detailed description of the preferred exemplary embodiments thereof.

DETAILED DESCRIPTION OF THE INVENTION

The term "late season" as used herein and in the accompanying claims is meant to refer to any time beyond peak flowering of a plant.

The preferred plant growth regulator in accordance with the present invention includes substituted semicarbazones and related compounds, such as thiosemicarcabazones and isothiosemicarbzones and salts thereof, as described more fully in U.S. Pat. Nos. 5,098,462 and 5,098,466 (the entire content of each U.S. patent being expressly incorporated hereinto by reference). The most preferred semicarbazone employed in the practice of this invention is diflufenzopyr.

The semicarbazone is applied to the locus of the plant in an amount sufficient to terminate continued reproductive growth of the plant. Most preferably, the semicarbazone is applied to the locus of the plant in an amount of at least about 0.0001, and typically at least about 0.003 pounds of active ingredient per acre (lb. ai/A). Furthermore, the semicarbazone is applied in amounts less than about 0.09, and usually less than about 0.03 lb ai/A.

The semicarbazones may be applied in the form of dusts, granules, solutions, emulsions, wettable powders, flowables and suspensions. Application of a compound as an active ingredient is made according to conventional procedure to the locus of the plant in need of the same using the appropriate amount of the compound per acre as will be described below. According to the present invention the application of the compound to the "locus" of the plant includes application to the plant or parts of the plant or the soil in which the plant is growing.

The semicarbazone compound may be applied to above ground portions of the plants. The application of liquid and particulate solid plant growth regulator compositions to above ground portions of plants may be carried out by conventional methods, for example, boom and hand application, including sprayers or dusters. The composition may be applied aerially as a spray, if desired. The semicarbazone compound employed in the practice of the present invention is most preferably used in the form of aqueous solutions. The solutions may be applied in a conventional manner, for example, by spraying, atomizing or watering the locus of the plant.

The semicarbazone compound may also be applied in conjunction with other ingredients or adjuvants commonly employed in the art. Examples of such ingredients include drift control agents, defoaming agents, preservatives, surfactants, fertilizers, phytotoxicants, herbicides, pesticides, insecticides, fungicides, wetting agents, adherents, nematocides, bactericides, trace elements, synergists, antidotes, mixtures thereof and other such adjuvants well known in the plant growth regulating art.

Regardless of the manner in which it is applied, the semicarbazone is applied to the locus of a crop plant in need of termination in an amount effective to terminate continued reproductive plant growth. The semicarbazone may be applied in single or multiple applications to the plant in order to obtain the desired early plant termination effects of this invention.

The present invention will be further illustrated by way of the following non-limiting examples.

EXAMPLE 1

Late-season application of diflufenzopyr (DFP) was field tested on cotton plants at the late-season growth stage described as "three nodes above white flower stage". It was surprisingly observed that diflufenzopyr caused a cessation of growth at the terminal (shoot apex) and promoted the abscission of flowers, squares and young bolls without causing significant injury to mature vegetative organs, intermediate-aged bolls and mature bolls. The results of these field trials are presented below in Table 1.

As seen therein, in Field Trial No. 1 (Mississippi), the results were striking. A single application of DFP at 0.01 or 0.02 lb. ai/A caused greater than 80% reductions (relative to untreated) in the number of both squares and flowers at the uppermost eight nodes. A similar trend was also observed in Field Trial No. 2 (Louisiana), although the magnitude of the reductions in the numbers of squares and flowers was not as large as in Field Trial No. 1. Together, these trials shown in Table 1 demonstrate that a low rate of semicarbazone, such as DFP, can drastically reduce the number of squares and flowers on a cotton plant.

TABLE 1

|  |  | Field Trial No. 1 (Mississippi) | | | | Field Trial No. 2 (Louisiana) | | | |
| --- | --- | --- | --- | --- | --- | --- | --- | --- | --- |
| Treatment | Rate (g/HA) | No. of Squares | % Decrease from Untreated | No. of Flowers | % Decrease from Untreated | No. of Squares | % Decrease from Untreated | No. of Flowers | % Decrease from Untreated |
| Untreated | — | 2.5 | — | 3.0 | — | 3.0 | — | 3.0 | — |
| DFP | 10 | 0.3 | 88 | 0.0 | 100 | 1.8 | 41 | 1.3 | 59 |
| DFP | 20 | 0.0 | 100 | 0.5 | 83 | 1.8 | 39 | 2.1 | 31 |

EXAMPLE 2

Another field trail was conducted in Mississippi, wherein DFP was applied to cotton plants at three nodes above white flower stage. The results are given in Table 2 below.

TABLE 2

|  |  | 22 Days After Treatment | |
| --- | --- | --- | --- |
| Treatment | Rate (g ai/ha) | No. of Open Bolls | % of Untreated |
| Untreated | — | 43 | 100 |
| DFP | 10 | 72 | 167 |
| DFP | 20 | 69 | 160 |

As is demonstrated from the data in Table 2, at the 20 g ai/ha rate, DFP-treated cotton plants had 60% more open bolls than the untreated plants at 22 days after treatment (DAT). This large increase in open bolls indicates that an application of DFP to cotton accelerates boll maturation which would translate into an earlier harvest for the cotton grower.

EXAMPLE 3

Greenhouse experiments were conducted using okra (*Abelmoschus esculentus*), a member of the same family (Malvaceae) as cotton. DFP application rates of 0.001 and 0.001 lb i/A did not affect okra growth (Table 3A). DFP application rates from 0.003 to 0.3 lb. ai/A dramatically reduced vegetative growth (Table 3B and 3C), and caused the abortion of flower buds and very small fruit (Tables 3D and 3E). The rate of fruit elongation in treated plants was slightly less than on untreated plants for the first week after application (Tables 3F and 3G). However, during the second week, the fruit on treated plants elongated at a faster rate than the fruit on the untreated plant so that by the end of two weeks, no significant difference was noted in fruit length. At the end of two weeks, plants treated with DFP had fewer fruit, but heavier fruit (Tables 5 3H and 3I).

Throughout the research described in the Tables below, there were between 5–10 okra plants per treatment, with the data for such treated okra plants being averaged.

TABLE 3A

Initial Screen Testing of DFP for Height Reduction in Okra

| Treatment | Rate (lb/ ai/A) | Okra Plant Height (cm) 14 DAT | % Phytotoxicity 14 DAT |
| --- | --- | --- | --- |
| Untreated | 0 | 33 | 0 |
| DFP | 0.0001 | 33 | 0 |
| DFP | 0.001 | 34 | 0 |
| DFP | 0.010 | 26 | 34 |

TABLE 3B

|  |  | Orka Plant Height | | |
| --- | --- | --- | --- | --- |
|  | Rate | Orka Plant Height (cm) | | % Decrease |
| Treatment | (lb/ ai/A) | 13 DAT | 28 DAT | 28 DAT |
| Untreated | 0 | 55 | 61 | — |
| DFP | 0.007 | 42 | 45 | 26 |
| DFP | 0.015 | 41 | 43 | 30 |
| DFP | 0.030 | 43 | 45 | 27 |

TABLE 3C

Okra Plant Height

| Treatment | Rate (lb/ ai/A) | Orka Plant Height (cm) 13 DAT | % Decrease |
| --- | --- | --- | --- |
| Untreated | 0 | 90 | — |
| DFP | 0.003 | 68 | 23 |
| DFP | 0.007 | 76 | 14 |

TABLE 3D

Fate of Orka Reproduction Organs That Were Either Flower Buds or Small Fruit at Application of DFP

|  |  | % Reduction in # of flower Buds | | % Reduction in # of Small Fruit | |
| --- | --- | --- | --- | --- | --- |
| Treatment | Rate (lb/ ai/A) | 6 DAT | 13 DAT | 6 DAT | 13 DAT |
| Untreated | 0 | 30 | 40 | 0 | 0 |
| DFP | 0.007 | 67 | 72 | 0 | 0 |
| DFP | 0.015 | 78 | 83 | 0 | 0 |
| DFP | 0.030 | 82 | 88 | 0 | 0 |

TABLE 3E

Fate of Orka Reproduction Organs That Were Either Flower Buds or Small Fruit at Application of DFP

| | | % Reduction in # of flower Buds | | % Reduction in # of Small Fruit | |
|---|---|---|---|---|---|
| Treatment | Rate (lb/ai/A) | 6 DAT | 13 DAT | 6 DAT | 13 DAT |
| Untreated | 0 | 9.4 | 30.2 | 0 | 0 |
| DFP | 0.003 | 61.1 | 48.1 | 0 | 0 |
| DFP | 0.007 | 57.1 | 53.1 | 31 | 23 |

TABLE 3F

Increase in Okra Fruit Length

| | Rate | Increase in Okra Pod Length (cm) | | |
|---|---|---|---|---|
| Treatment | (lb/ai/A) | 0–6 DAT | 6–13 DAT | 0–13 DAT |
| Untreated | 0 | 11.3 | 0.1 | 11.2 |
| DFP | 0.007 | 6.6 | 4.3 | 10.9 |
| DFP | 0.015 | 7.3 | 2.4 | 9.7 |
| DFP | 0.030 | 7.6 | 3.1 | 10.6 |

TABLE 3G

Increase in Okra Fruit Length

| | Rate | Increase in Okra Pod Length (cm) | | |
|---|---|---|---|---|
| Treatment | (lb/ai/A) | 0–6 DAT | 6–13 DAT | 0–13 DAT |
| Untreated | 0 | 11.9 | 1.2 | 13.1 |
| DFP | 0.003 | 10.2 | 1.7 | 11.9 |
| DFP | 0.007 | 10.4 | 1.7 | 13.1 |

TABLE 3H

Orka Yield of Fruit as Weight in Grams

| | Rate | Okra Fruit Wt. (gm) at 13 DAT | | % Increase Fruit Wt. | |
|---|---|---|---|---|---|
| Treatment | (lb/ai/A) | fresh wt. | dry wt. | fresh wt. | dry wt. |
| Untreated | 0 | 21.8 | 3.07 | — | — |
| DFP | 0.007 | 30.0 | 3.63 | 37 | 18 |
| DFP | 0.015 | 29.3 | 3.53 | 34 | 15 |
| DFP | 0.030 | 35.2 | 4.17 | 61 | 36 |

TABLE 3I

Orka Yield of Fruit as Weight in Grams*

| | Rate | Orka Fruit Dry Wt. (gm) by Fruition Position | | | |
|---|---|---|---|---|---|
| Treatment | (lb/ai/A) | Position 1 | Position 2 | Position 3 | Position 4 |
| Untreated | 0 | 21.8 | 3.07 | — | — |
| DFP | 0.007 | 30.0 | 3.63 | 37 | 18 |
| DFP | 0.15 | 29.3 | 3.53 | 34 | 15 |

*Pods were harvested at 13 DAT. At application position 1 was the lowest and largest fruit on the plant, position 2 was the next oldest fruit, etc.

The data above demonstrate that a single application of a semicarbazone, such as diflufenzopyr at a rate range between about 0.003 to about 0.03 lb. ai/A to a crop plant, such as cotton or okra, can cause the abscission of flower buds, flowers and young fruit as well as dramatically reduce vegetative growth. Surprisingly, the weight of the okra fruit was increased by treatments with DFP.

EXAMPLE 4

Field trials were conducted on peanut plants (*Arachis hypogaea*) to determine if late season applications of DFP could stop the development of late season flowers and vegetative growth. Applications of DFP were made using a $CO_2$ back-pack sprayer calibrated to deliver 10 gallons/acre (gpa). Ground plots containing the peanut plants were 12 feet×50 feet. Applications were targeted to be made to actively growing peanut plants approximately six (6) weeks and three (3) weeks prior to harvest. Applications of DFP with 1% v/v DASH® HC spray adjuvant were applied broadcast to peanut. Peanuts were collected and weighed to calculate yield data shown in Table 4 below. All trials were irrigated, except for the GA-015 trial which was conducted under drought conditions. DFP was applied at rates of 0.007 and 0.015 lb. ai/A.

TABLE 4

Peanut yield expressed as percent of the untreated check.

| | Rate lb | | Peanut Yield as % of untreated check | | | |
|---|---|---|---|---|---|---|
| Treatment | ai/acre | Timing* | GRS-287 | FTS | NC-101 | GA-015 |
| Untreated | — | — | 100 | 100 | 100c | 100 |
| DFP | 0.007 | 6 wk | 107 | 102 | 111 | 98 |
| DFP | 0.015 | 6 wk | 92 | 104 | 115 | 89 |
| DFP | 0.030 | 6 wk | 89 | 99 | 127 | 92 |
| DFP | 0.007 | 3 wk | 107 | 109 | 130 | 87 |
| DFP | 0.015 | 3 wk | 102 | 110 | 122 | 99 |
| DFP | 0.030 | 3 wk | 78 | 108 | 118 | 104 |

Notes:
(1) GRS-287 - Interval between applications and harvest was 68 and 45 days.
(2) FTS - Interval between applications and harvest was 55 and 35 days.
(3) NC-101 - Interval between applications and harvest was 42 and 32 days.
(4) GA-015 - Interval between application and harvest was 45 and 32 days.

Some peanut injury was observed and was dependent on the rate of DFP application. Thus, as the rate of DFP increased, peanut injury also increased. By 31 DAT, however, peanut injury was not significant. Injury symptoms included slight curling of the upper most leaves within the peanut canopy. DFP applied at 0.030 lb ai/A produced the most injury at approximately 20%, but the peanut injury did not include noticeable chlorosis.

As evident in the data of Table 4, significant yield increase was observed at the NC-101 trials. Significant yield increases occurred form applications of DFP applied six weeks prior to harvest at 0.030 lb ai/A and DFP applied three weeks prior to harvest at 0.007, 0.015 and 0.030 lb ai/A. As seen in note (3) to Table 4, the NC-101 trial most nearly estimated the time from application to harvest of all the studies. At the GRS and FTS trials, however, the lower application rates (0.007 and 0.015 lb ai/A) applied at the second date increased yields by the statistically insignificant amounts of 2% to 10%. The GA-015 trial, however, resulted in no trend toward increased yield which was not unexpected due to the drought stress the plants were under for much of the trial season.

EXAMPLE 5

Additional field trials were conducted on cotton plants (variety DPL 50) to determine if the size of bolls that are aborted by DFP application are affected by stress, excessive application rates or the timing of application. Specifically, a mixture of DFP with 1% v/v DASH® HC spray adjuvant was applied at rates of 0.01, 0.02 and 0.08 lb ai/A at 5 nodes above white flower (5 NAWF), corresponding to 40 days before defoliation, 5 NAWF+300 DD, corresponding to 25 days before defoliation, and 5 NAWF+600 DD, corresponding to 15 days before defoliation. The results appear in Table 5 below.

When applied at 5 NAWF to non-stressed cotton, retention of mature bolls tended to increase as the DFP rate increased. DFP application had no influence on the retention of mature bolls when applied at the later timings. DFP application caused cotton to shed squares and flowers at all rates and timings evaluated. At the 600 DD timing, virtually all immature squares were shed and flowering had terminated. Thus, an yield increase at this time is probably due to improving the efficiency of carbohydrate utilization by the

TABLE 5

|  | Timing | Rate (lb ai/A) | Shed Bolls | Avg. Boll Size (mm) | Avg. Boll Size (inches) | Yield Bales/A | Conditions |
|---|---|---|---|---|---|---|---|
| Untreated |  |  | 65 | 22.5 | 0.8 | 2.06 | non stressed |
| DFP | 5 NAWB | 0.010 | 57 | 20.5 | 0.8 | 1.27 | " |
| " | " | 0.020 | 53 | 20.6 | 0.8 | 1.2 | " |
| " | " | 0.080 | 42 | 18.6 | 0.7 | 1.1 | " |
| " | 300 DD | 0.010 | 43 | 22.9 | 0.9 | 1.9 | " |
| " | " | 0.020 | 60 | 21.8 | 0.8 | 1.9 | " |
| " | " | 0.080 | 43 | 20.8 | 0.8 | 1.8 | " |
| " | 600 DD | 0.010 | 32 | 21.9 | 0.8 | 2.19 | " |
| " | " | 0.020 | 35 | 27.7 | 1.09 | 2.14 | " |
| " | " | 0.080 | 61 | 27.9 | 1.09 | 2.11 | " |
| Untreated |  |  | 31 | 12.3 | 0.4 | 1.86 | Stressed |
| DFP | 5 NAWB | 0.010 | 32 | 18.5 | 0.7 | 1.38 | " |
| " | " | 0.020 | 53 | 18.8 | 0.74 | 1.24 | " |
| " | " | 0.080 | 64 | 20.5 | 0.8 | 1.25 | " |
| " | 300 DD | 0.010 | 47 | 14.6 | 0.5 | 1.96 | " |
| " | " | 0.020 | 58 | 29.2 | 1.14 | 1.8 | " |
| " | " | 0.080 | 50 | 23 | 0.9 | 1.77 | " |
| " | 600 DD | 0.010 | 49 | 24.8 | 1 | 1.99 | " |
| " | " | 0.020 | 35 | 21.4 | 0.8 | 2.08 | " |
| " | " | 0.080 | 33 | 24.8 | 0.9 | 2.01 | " |

As apparent from the data in Table 5 above, the timing of the DFP application had a more dramatic effect on yield than did the application rate. The 0.01 and 0.02 lb. ai/A rates tended to have less of a negative effect on yield at each timing as compared to the 0.80 lb ai/A rate. Applications at 5 NAWF significantly reduced yields as compared to the untreated check at the 5% level. Surprisingly, all treatments at the 667 DD timing tended to increase yields. The 0.01 and 0.02 lb. ai/A rates marginally provided significant yield increases at the 5% level. At the 10% level, DFP application at a rate of 0.20 lb. ai/A provided a significant yield increase. Only the 0.080 lb. ai/A application rate caused a significant yield reduction at the 300 DD application timing.

plant. No negative effect on seed germination or quality at the 300 DD or 600 DD timings was observed. However, a tendency to cause a negative effect on seed germination and quality was observed at DFP treatment at 5 NAWF. Therefore, the most practical application timing in cotton appears to be after the 5 NAWF stage.

EXAMPLE 6

Example 5 was repeated at another test site. The results appear in Table 6 below.

TABLE 6

|  | Timing | Rate (lb ai/A) | Shed Bolls | Avg. Shed Boll Size (mm) | Yield Bales/A | Conditions |
|---|---|---|---|---|---|---|
| Untreated |  |  | 1.19 | 0.81 | 1.78 | non stressed |
| DFP | 5 NAWB | 0.010 | 2.29 | 1.75 | 1.46 | " |
| " | " | 0.020 | 2.56 | 2.33 | 1.07 | " |
| " | " | 0.080 | 3.90 | 2.25 | 0.69 | " |
| " | 300 DD | 0.010 | 1.17 | 1.38 | 1.63 | " |
| " | " | 0.020 | 1.83 | 1.61 | 1.64 | " |
| " | " | 0.080 | 1.76 | 1.60 | 1.67 | " |
| " | 600 DD | 0.010 | 0.17 | 0.60 | 1.72 | " |
| " | " | 0.020 | 0.17 | 0.16 | 1.81 | " |
| " | " | 0.080 | 0.17 | 0.61 | 1.87 | " |
| Untreated |  |  | 1.11 | 0.65 | 2.03 | Stressed |
| DFP | 5 NAWB | 0.010 | 2.28 | 0.97 | 1.77 | " |
| " | " | 0.020 | 3.29 | 1.38 | 1.62 | " |
| " | " | 0.080 | 4.00 | 1.78 | 1.58 | " |
| " | 300 DD | 0.010 | 0.61 | 1.07 | 2.08 | " |

TABLE 6-continued

| Timing | Rate (lb ai/A) | Shed Bolls | Avg. Shed Boll Size (mm) | Yield Bales/A | Conditions |
|---|---|---|---|---|---|
| " | " | 0.020 | 0.41 | 0.94 | 2.27 | " |
| " | " | 0.080 | 0.61 | 0.83 | 2.03 | " |
| " | 600 DD | 0.010 | 0.31 | 0.31 | 2.29 | " |
| " | " | 0.020 | 0.26 | 0.26 | 2.14 | " |
| " | " | 0.080 | 0.37 | 0.37 | 2.22 | " |

Example 7

DFP was applied at 0.01 and 0.02 lb ai/A on cotton at two different growth stages: 5 NAWF and 5 NAWF+350 HU (Heat Units) on the variety Stoneville 474. The results appear in Tables 7A and 7B, below therefore indicate that DFP at 0.02 lb ai/A has a great potential as a cotton plant termination aid.

EXAMPLE 8

DFP treatments were applied to tobacco plants in a commercial, flue cured tobacco field. Plants were topped and

TABLE 7A

Efficacy of DFP For Insect Control Applied at 5 NAWF Stage

| | | | Eval. No. | | | | | | | | |
|---|---|---|---|---|---|---|---|---|---|---|---|
| Variable DAT | | | 1 YFDRO1[2] | 1 YFDRO2 | 1 YFDRO3 | 1 YFDRO4 | 1 YFDRO5 | 2 LYGUL[3] | 2 HELISP | 3 LYGULI | 3 HELISP | 3 YOBOLL |
| Treatment | | Rate[1] | 15 | 15 | 15 | 15 | 15 | 17 | 17 | 21 | 21 | |
| Untreated | | | 0.3a[4] | 8.3a | 1.5b | 2.5b | 0b | 5.8a | 0.3a | 7.8a | 3.5a | 5.5a |
| BAS 131 | UA W WG | 0.01 lb ai/A | 0a | 4a | 4.3ab | 9.5ab | 41.3a | 2.8a | 0.3a | 4.5a | 2.5a | 5.5a |
| BAS 131 | UA W WG | 0.01 lb ai/A | 0a | 1a | 5.8a | 10.5a | 37a | 5.5a | 0.8a | 11.5a | 6.5a | 10.8a |

[1]Product delivered at 200 l/ha.
[2]YFDRO1 = number dropped bolls <¼inch diameter/25 ft. of row.
YFDRO2 = number dropped bolls <¼><½inch diameter/25 ft. of row.
YFDRO3 = number dropped bolls <½><¾inch diameter/25 ft. of row.
YFDRO4 = number dropped bolls <¾><1 inch diameter/25 ft. of row.
YFDRO5 = number dropped bolls <1 inch diameter/25 ft. of row.
[3]Mean number tarnished plant bug nymphs (LYGULI), boll/budworm larvae (RELISP), and boll weevil punctured squares (YOBOLL)/50 squares
[4]Means followed by the same letter are not significantly different by Duncan's Multiple Range Test (P = 0.05).

TABLE 7B

Efficacy of DFP For Insect Control Applied at 5 NAWF Plus 350 HU Stage

| Eval. No. Variable DAT Treatment | | Rate lb ai/A | 1 LYGULI 14 | 1 YOBOLL 14 | 1 HELISP 14 | 2 LYGULI 21 | 2 YOBOLL 21 | 2 HELISP 21 | 3 LYGULI 28 | 3 YOBOL 28 | 3 HELISP 28 |
|---|---|---|---|---|---|---|---|---|---|---|---|
| Untreated | | | 2.3ab3 | 7.8a | 3a | 7.8a | 22.5a | 0.8a | 2.8a | 10.0a | 1.3a |
| BAS 131 | UA W | 0.01 | 4.3a (—)[4] | 7.8a (—) | 3.3a (—) | 5.3a (32) | 12ab (47) | 2.5A (—) | 1.8a (36) | 10.8a | 1.3a |
| BAS 131 | UA W | 0.02 | 1b (56) | 5.8a (56) | 1.5a (50) | 3.3a (58) | 9.5b (58) | 2a (—) | 2.3a (18) | 10.0a | 1.8a |

[1]Product delivered at 200 l/ha.
[2]Mean number tarnished plant bug nymphs (LYGULI), boll weevil punctured squares (YOBOLL), and boll/budworms (HELISP) per ≦/50 squares/plot.
[3]Means followed by the same letter are not significantly different by Duncan's Multiple Range Test (P = 0.05).
[4]% Reduction as compared to the check.

The data above indicate that application at the 5 NAWF stage did not result in sufficient square shed to reduce insect populations and caused the cotton to drop a significant number of bolls greater than 1 inch in diameter. At the second timing of 5 NAWF+350 HU, however, plots treated with DFP at 0.02 lb ai/A showed significant reductions in punctured squares by boll weevils (58%) and tarnished plant bug nymphs (32%) as compared to the untreated check. At this later timing, no boll shed was observed. These results sprayed on the same day. About 5–10% of the tobacco plants were at the bud stage at application. Treatments were applied with a hand-held sprayer equipped with a hollow cone nozzle. Spray volume was 33 ml per plant or roughly 50 gallons per acre. Each treatment was applied to the three tobacco plants and each plant was considered a replication. The plants were examined at various intervals measured in weeks after treatment (WAT). One treatment, the commercial standard Royal MH-30 (maleic hydrazide) applied at 3.0 lbs. ai/A, could not be applied until the following day. Because of this delay in application, the treatment was not significantly different from the check and are not included in the results below in Tables 8A–8C.

TABLE 8A

Percent injury on flue-cured tobacco

| Treatment | Lbs ai/A | Percent Injury | |
|---|---|---|---|
| | | 1 WAT | 3 WAT |
| Untreated | 0 | 0 | 0 |
| BAS 131W | 0.01 | 25 | 10 |
| BAS 131W | 0.03 | 40 | 35 |
| BAS 131W + MH-30 | 0.01 + 1.0 | 25 | 20 |
| BAS 131W + MH-30 | 0.03 + 1.0 | 40 | 25 |
| MH-30 | 1.0 | 0 | 0 |

TABLE 8B

Number of Suckers/plant on flue-cured tobacco

| | Lbs ai/A | Number of Suckers per Plant | | | |
|---|---|---|---|---|---|
| | | 1 WAT | 3 WAT | 4 WAT | 6 WAT |
| Untreated | 0 | 3.0 | 3.0 | 4.3 | 8.5 |
| BAS 131W | 0.01 | 0 | 2.7 | 6.3 | 7 |
| BAS 131W | 0.03 | 0 | 0 | 4.5 | 10 |
| BAS 131W | 0.06 | 0 | 0 | 2.0 | 4.5 |
| BAS 131W + MH-30 | 0.01 + 1.0 | 0 | 0.3 | 4.0 | 5.3 |
| BAS 131W + MH-30 | 0.03 + 1.0 | 0 | 0.3 | 2.3 | 6.3 |
| MH-30 | 1.0 | 0 | 1.0 | 5.7 | 5.3 |

TABLE 8C

Total sucker weight per plant, average sucker weight and length and the length of the top five tobacco leaves at the final evaluation at 41 days after treatment (DAT)

| | Lbs. ai/A | Total Sucker wt./ plant | Avg. Sucker wt. (gm) | Avg. Sucker length (cm) | Avg. Length of Top 5 leaves |
|---|---|---|---|---|---|
| Untreated | 0 | 715 | 82 | 28 | 62 |
| BAS 131W | 0.01 | 217 | 32 | 23 | 58 |
| BAS 131W | 0.03 | 270 | 27 | 15 | 53 |
| BAS 131W | 0.06 | 100 | 15 | 15 | 57 |
| BAS 131W + MH-30 | 0.01 + 1.0 | 123 | 21 | 14 | 59 |
| BAS 131W + MH-30 | 0.03 + 1.0 | 176 | 32 | 17 | 63 |
| MH-30 | 1.0 | 226 | 49 | 23 | 68 |

The data above shows that DFP produced some injury symptoms on immature leaves of typical auxin accumulation (see Table 8A) which was evidenced by leave curling. In addition, these leaves undesirably stayed greener late in the season. The injury did not, however, reduce the final length of the top five leaves at harvest (see Table 8C, but there was a slight trend toward decrease length. Mature leaves did not show injury symptoms. DFP did reduce the number of suckers per plant with the highest rate of 0.06 lbs ai/A being effective at six weeks after application (Table 8B). Lower rates of DFP were effective for shorter periods of time. Once the inhibitory activity of DFP ceased, the sucker number quickly rebounded. The combination of DFP with a 1.0 pound rate of maleic hydrazide was not significantly different from DFP alone. At 6WAT, all treatments reduced sucker weight per plant and average sucker weight (see Table 8C). DFP at 0.6 lbs ai/A was the most effective treatment in reducing total sucker weight per plant, average sucker weight and average sucker length.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for the late season termination of reproductive crop plant growth of a plant comprising applying to a locus of a plant at a time following peak bloom of the plant a sufficient amount of a semicarbazone plant growth regulator to terminate continued reproductive growth of the plant.

2. The method of claim 1, wherein the plant is one having an indeterminate growth pattern.

3. The method of claim 1, wherein the semicarbazone plant growth regulator is sufficient to terminate continued reproductive growth without substantially affecting mature reproductive growth existing on the plant at the time of application.

4. The method of claim 1, wherein the plant is of the Malvaceae or Fabaceae family.

5. The method of claim 4, wherein the plant is a cotton, okra or peanut plant.

6. The method of claim 1, wherein the semicarbazone is diflufenzopyr.

7. The method of claim 6, wherein the application rate of diflufenzopyr is between about 0.0001 to about 0.09 pounds of active ingredient per acre.

8. The method of claim 7, wherein the application rate is between about 0.003 to about 0.03 pounds active ingredient per acre.

9. The method of claim 1, wherein the semicarbazone is applied together with at least one adjuvant.

10. The method of claim 1, wherein the semicarbazone is applied in the form of a liquid or a solid particulate.

11. The method of claim 1, wherein the plant is cotton, and wherein the semicarbazone is applied to the cotton plant at three nodes above white flower stage.

12. The method of claim 11, wherein the semicarbazone is diflufenzopyr.

13. The method of claim 1, wherein the plant is *Nicotiana tabacum L.*

\* \* \* \* \*